United States Patent
Levon et al.

(10) Patent No.: US 10,370,694 B2
(45) Date of Patent: Aug. 6, 2019

(54) SIZE DEPENDENCE OF NANOPARTICLE-PROTEIN INTERACTION AND HIGH SENSITIVITY POTENTIOMETRIC SENSOR EXPLOITING SUCH INTERACTIONS

(71) Applicant: New York University, New York, NY (US)

(72) Inventors: Kalle Levon, Brooklyn, NY (US); Yanyan Wang, Tianjin (CN)

(73) Assignee: New York University, New York, NY (US)

( * ) Notice: Subject to any disclaimer, the term of this patent is extended or adjusted under 35 U.S.C. 154(b) by 85 days.

(21) Appl. No.: 15/156,648

(22) Filed: May 17, 2016

(65) Prior Publication Data
US 2016/0341686 A1  Nov. 24, 2016

Related U.S. Application Data

(60) Provisional application No. 62/163,707, filed on May 19, 2015.

(51) Int. Cl.
| | |
|---|---|
| *G01N 27/327* | (2006.01) |
| *C12Q 1/00* | (2006.01) |
| *C25D 3/48* | (2006.01) |
| *C25D 5/18* | (2006.01) |

(Continued)

(52) U.S. Cl.
CPC .............. *C12Q 1/006* (2013.01); *C25D 3/48* (2013.01); *C25D 5/18* (2013.01); *G01N 27/3278* (2013.01); *B82Y 30/00* (2013.01); *C25D 5/54* (2013.01)

(58) Field of Classification Search
CPC ...... C12Q 1/006; G01N 27/3278; C25D 5/18; C25D 3/48; C25D 5/54; B82Y 30/00
See application file for complete search history.

(56) References Cited

PUBLICATIONS

Qu, et al. (Electrochemical Synthesis of Gold Nanoparticles in Polypyrrole for Antibody Immobilization Proceedings of the 2009 4th IEEE International Conference on Nano/Micro Engineered and Molecular Systems, Jan. 5-8, 2009, p. 597-600 (Year: 2009).*

(Continued)

*Primary Examiner* — J. Christopher Ball
(74) *Attorney, Agent, or Firm* — John C. Pokotylo; Pokotylo Patent Services

(57) ABSTRACT

Fabrication of a high sensitivity potentiometric biosensor is described. The present inventors have developed and characterized a novel amplification platform using a gold nanoparticle (GNPs) electrodeposition method. The synthesized GNP sizes were found to be dependent of $HAuCl_4$ concentration, media acid, scan cycles and scan rate. A systematic investigation into the adsorption of different sizes of proteins from aqueous electrolyte solution onto the electrodeposited GNPs surface by the potentiometric method was performed. Results suggest that the size of different proteins affect how they bond to different sizes of GNPs. This GNPs-based biosensor can retain the native-like structure of proteins, and successfully detect proteins at a high sensitivity level. The resulting glucose and immune biosensors also exhibit low detection limit and wide linear range. This improvement to potentiometric devices enables them to serve as highly sensitive detectors for biomolecules and provides a model that can be used to predict protein bonding on nanoparticles.

10 Claims, 12 Drawing Sheets

(51) Int. Cl.
C25D 5/54 (2006.01)
B82Y 30/00 (2011.01)

(56) References Cited

PUBLICATIONS

S. R. Saptarshi, et al. "Interaction of nanoparticles with proteins: relation to bio-reactivity of the nanoparticle" Journal of Nanobiotechnology, 11( 1 ): p. 26+, Jul. (Year: 2013).*

M. S. El-Deab, et al. "Size and crystallographic orientation controls of gold nanoparticles electrodeposited on GC electrodes", Journal of the Electrochemical Society, 152(1): p. C1-C6, Jan. (Year: 2005).*

* cited by examiner

SIZE DEPENDENCE OF NANOPARTICLE-PROTEIN INTERACTION AND HIGH SENSITIVITY POTENTIOMETRIC SENSOR EXPLOITING SUCH INTERACTIONS

§ 0. RELATED APPLICATIONS

This application claims benefit to U.S. Provisional Application Ser. No. 62/163,707, titled "SIZE DEPENDENCE OF NANOPARTICLE-PROTEIN INTERACTION AND HIGH SENSITIVITY POTENTIOMETRIC SENSOR EXPLOITING SUCH INTERACTIONS," filed on May 19, 2015, and listing Kalle Levon and Yanyan Wang as the inventors (referred to as "the '707 provisional" and incorporated herein by reference). The scope of the present invention is not limited to any requirements of the specific embodiments described in '707 provisional.

§ 1. BACKGROUND OF THE INVENTION

§ 1.1 Field of the Invention

The present invention concerns potentiometric biosensors, and methods for making potentiometric biosensors.

§ 1.2 Background Information

Potentiometry is a measurement method that monitors the potential difference between working electrode and reference electrode. Nowadays, potentiometric device such as field effect transistor (FET) and light—addressable potentiometric sensor (LAPS) are the most popular electrical biosensors (See, e.g., the articles, Schoning, M. J. and A. Poghossian, "*Bio FEDs (Field-Effect Devices): State-of-the-Art and New Directions,*" Electroanalysis, 2006. 18(19-20): p. 1893-1900 and Robert, K., "*Recent Developments in Potentiometric Biosensors for Biomedical Analysis,*" Analytica Chimica Acta, 2007. 599(1): p. 7-15 (incorporated herein by reference).) These kinds of label free sensors with potentiometric signal generation and transduction, are of great interest because they would not only significantly decrease the cost and time needed for sample preparation but would also eliminate issues related to modification of target molecules, which is desirable for effective clinical diagnostics.

A great amount of research has been reported about investigating protein or DNA adsorption to the surface of potentiometric device and about real time monitoring the potential response which depend on the intrinsic charges that the proteins or DNA carry (See, e.g., the articles, Robertson, J., "*High Dielectric Constant Gate Oxides for Metal Oxide Si Transistors,*" Reports on Progress in Physics, 2006. 69(2): p. 327-396, Gao, Z. Q., et al., "*Silicon Nanowire Arrays for Label-Free Detection of DNA,*" Analytical Chemistry, 2007. 79(9): p. 3291-3297, Maehashi, K., et al., "*Label-Free Protein Biosensor Based on Aptamer-Modified Carbon Nanotube Field-Effect Transistors,*" Analytical Chemistry, 2007. 79(2): p. 782-787 and Kuga, S., et al., "*Detection of Mismatched DNA on Partially Negatively Charged Diamond Surfaces by Optical and Potentiometric Methods,*" Journal of the American Chemical Society, 2008. 130(40): p. 13251-13263 (incorporated herein by reference).) However, there still exist challenges when it comes to the real medical application of the potentiometric based biosensor. First, the concept regarding "Debye screening length" should be taken into consideration (See, e.g., the articles Stern, E., et al., "*Importance of the Debye Screening Length on Nanowire Field Effect Transistor Sensors,*" Nano Letters, 2007. 7(11): p. 3405-3409 and Sorgenfrei, S., et al., "*Debye Screening in Single-Molecule Carbon Nanotube Field-Effect Sensors,*" Nano Letters, 2011. 11(9): p. 3739-3743 (incorporated herein by reference).). Debye length is the distance over which the moving charge carriers screen out the external electric field. In the physiological solution, charged proteins will be surrounded by opposite of charged ions due to electrostatic interactions. If the proteins recognition take place at the distance beyond a Debye length from sensing platform, resulting the electrostatic potential which arising from charges on the proteins decays exponentially toward zero with distance (See, e.g., the article Stern, E., et al., "*Importance of the Debye Screening Length on Nanowire Field Effect Transistor Sensors,*" Nano Letters, 2007. 7(11): p. 3405-3409 (incorporated herein by reference).) For this reason, the potentiometric measurements can only sense biomolecules within the Debye length. Thus the diagnostic monitoring might be restricted because biomolecular interaction events, like protein-protein interactions usually occur beyond approximately 2-12 nm from the detection surface due to the height of the proteins (See, e.g., the articles, Lee, C.-S., S. Kim, and M. Kim, "*Ion-Sensitive Field-Effect Transistor for Biological Sensing,*" Sensors 2009. 9(9): p. 7111-7131 and Lee, K. K., C. A. Fitch, and B. García-Moreno E, "*Distance Dependence and Salt Sensitivity of Pairwise, Coulombic Interactions in a Protein,*" Protein Science, 2002. 11(5): p. 1004-1016 (incorporated herein by reference).) Therefore, this Debye screening length has become one of the main disadvantages in measuring the biomolecular recognition using potentiometry-type biosensor. Second, the need for rapidly, selectively and highly sensitive sense trace concentrations of specific disease diagnosis markers that present at ultralow levels during early stages of disease progression, such as proteins, DNA sequences, is critical for clinical diagnostics. Thus, a highly sensitive and selective potentiometric sensor should be developed.

To overcome these problems, several approaches have been attempted. Such as increasing Debye length by the use of low capacity buffer solutions (See, e.g., the article, Volotovsky, V., et al., "*Glucose-Sensitive Ion-Sensitive Field-Effect Transistor-Based Biosensor with Additional Positively Charged Membrane. Dynamic Range Extension and Reduction of Buffer Concentration Influence on the Sensor Response,*" Analytica Chimica Acta, 1996. 322(1-2): p. 77-81 (incorporated herein by reference).); adding a charged polymeric membrane blocking the buffer—mediated facilitated transport of ions out of the film resulting in an increasing in the signal response (See, e.g., the articles, Dzyadevich, S. V., et al., "*Application of Enzyme Field-Effect Transistors for Determination of Glucose Concentrations in Blood Serum,*" Biosensors and Bioelectronics. 1999. 14(3): p. 283-287 and Ding, J. and W. Qin, "*Current-Driven Ion Fluxes of Polymeric Membrane Ion-Selective Electrode for Potentiometric Biosensing,*" Journal of the American Chemical Society, 2009. 131(41): p. 14640-14641 (incorporated herein by reference).) and using enzymes—labeled secondary antibodies in a sandwich structure on the analyte resulting in the development of enzyme immunoassay in the biosensor format (See, e.g., the articles, Wu, J., et al., "*Potentiometric Detection of DNA Hybridization Using Enzyme-Induced Metallization and a Silver Ion Selective Electrode,*" Analytical Chemistry, 2009. 81(24): p. 10007-10012 and Numnuam, A., et al., *Aptamer-Based Potentiometric Measurements of Proteins Using Ion-Selective Microelectrodes,*" Analytical Chemistry, 2008. 80(3): p.

707-712 (incorporated herein by reference).) In spite of what progresses have been achieved so far, there is not yet sufficient experimental data on the construction of label free potentiometric based biosensors with a simple and smart substrate that will be able to detect biomolecules with high sensitivity in the solution of high ionic strength like physiological fluid. Achieving an exciting substrate with very high sensitivity plays a pivotal role in biological detection.

For high sensitivity determination of biomolecules in physiological fluid, two major challenges are of key importance: (i) amplification platform and (ii) amplification process. So far, most of those reported researches mainly use the method of amplification process that use nanoparticles as labels for signal amplification because of their unique electronic, catalytic and optical properties (See, e.g., the articles, Rosi, N. L. and C. A. Mirkin, "*Nanostructures in Biodiagnostics,*" *Chemical Reviews*, 2005. 105(4): p. 1547-1562, Shipway, A. N., E. Katz, and I. Willner, "*Nanoparticle Arrays on Surfaces for Electronic, Optical, and Sensor Applications,*" *Chemphyschem*, 2000. 1(1): p. 18-52 and Brannon-Peppas, L. and J. O. Blanchette, "*Nanoparticle and Targeted Systems for Cancer Therapy,*" *Advanced Drug Delivery Reviews*, 2004. 56(11): p. 1649-1659 (incorporated herein by reference).). For using metal nanoparticle as amplification platform, various approaches including self-assembly or grafting reaction etc were achieved. But a problem for those methods is that the preparation of nanoparticle film with over than 25% surface coverage is difficult due to the repulsive force between surface-confined nanoparticles and free nanoparticles in solution (See, e.g., the article, Grabar, K. C., et al., "*Kinetic Control of Interparticle Spacing in Au Colloid-Based Surfaces: Rational Nanometer-Scale Architecture,*" *Journal of the American Chemical Society*, 1996. 118(5): p. 1148-1153 (incorporated herein by reference).) The method of electrochemical deposition provides an easy and rapid alternative for preparation of nanoparticle platform in a short time. Among the nanoparticles, gold nanoparticles (GNPs) can be easily conjugated with biomolecules and retain the biochemical activity of tagged biomolecules, leading GNPs to be attractive materials for biorecognition application (See, e.g., the article, Cao, X., Y. Ye, and S. Liu, "*Gold Nanoparticle-Based Signal Amplification for Biosensing,*" *Analytical Biochemistry*, 2011. 417 (1): p. 1-16 (incorporated herein by reference).). The characterization of GNPs such as electron dense core, high surface to volume ratio, conductivity and electrochemical properties have made GNPs been widely used as sensitive tracers for biomolecular recognition events (See, e.g., the articles, Wang, J., "*Nanomaterial-Based Amplified Transduction of Biomolecular Interactions,*" *Small*, 2005. 1(11): p. 1036-1043 and Guo, S. J. and E. K. Wang, "*Synthesis and Electrochemical Applications of Gold Nanoparticles,*" *Analytica Chimica Acta*, 2007. 598(2): p. 181-192 (incorporated herein by reference).). Thus, in this work, the GNP was selected to form a thin film on the substrate of electrode with electrodeposited method, to act as an amplification platform for high sensitivity detection of biomolecules with potentiometric methods.

Furthermore, the size of nanoparticle has substantial effects on protein structure and stability compared to relatively 'flat' supports (See, e.g., the article, Gagner, J. E., et al., "*Effect of Gold Nanoparticle Morphology on Adsorbed Protein Structure and Function,*" *Biomaterials*, 2011. 32(29): p. 7241-7252 (incorporated herein by reference).). For the flat substrates with nanoscale roughness, the effect of GNPs size on protein interaction has not been studied in detail. Here, we chose three kinds of proteins of with distinct sizes, but similar isoelectric point (pI) values: Bovine serum albumin (BSA) is a triangular prismatic protein with a size of 14 nm×4 nm×4 nm (Mw 66.3 kDa, pI=4.8); Glucose oxidase (GOx), a dimeric globular protein having overall dimensions of 6×5.2×7.7 nm (Mw 160 kDa, pI=4.2) (See, e.g., the article, Libertino, S., et al., "*Immobilization of the Enzyme Glucose Oxidase on Both Bulk and Porous SiO2 Surfaces,*" *Sensors* 2008. 8(9): p. 5637-5648 (incorporated herein by reference).); and casein proteins involved four types of proteins, alpha(s1)-casein (38%), alpha(s2)-casein (10%), casein (36%) and kappa-casein (13%), which form hydrated casein micelles about 100-300 nm in size (pI=4.6) (See, e.g., the article, Horne, D. S., *Casein interactions: "Casting Light on the Black Boxes, the Structure in Dairy Products,*" *International Dairy Journal*, 1998. 8(3): p. 171-177 (incorporated herein by reference).). Films of GNPs with different sizes were fabricated to study the influence of the sizes of these three proteins to the electrode surface.

§ 2 SUMMARY OF THE INVENTION

The challenge of making a potentiometric biosensor including a specific protein adsorbed onto a nanoparticle surface, is solved by (a) depositing nanoparticles onto an electrode to produce a nanoparticle modified electrode, such that a mean size of the deposited nanoparticles corresponds to a size promoting immobilization of the specific protein onto the nanoparticles without denaturing the specific protein whereby the specific protein remains active after being immobilized onto the nanoparticles; and (b) adsorbing the specific protein onto the nanoparticle electrode to produce the potentiometric biosensor.

In some example embodiments consistent with the present invention, gold nanoparticle is electrodeposited onto an electrode to produce a gold nanoparticle modified electrode, wherein the electrodepositing uses electrodeposition parameters selected to deposit gold nanoparticles on the electrode such that a mean size of the deposited gold nanoparticles corresponds to a size promoting adsorption of the specific protein onto the gold nanoparticles.

In some example embodiments consistent with the present invention, the electrodepositing is performed using cyclic voltmmetry electrodeposition. In some such example embodiments consistent with the present invention, at least one of the electrodepostion parameters is acidic solution concentration, a voltage scan rate, and/or a maximum number of scan cycles.

In some example embodiments consistent with the present invention, the specific protein is Bovine serum albumin (BSA) and the mean size of the deposited gold nanoparticles is 5 nm±2 nm. In other example embodiments consistent with the present invention, the specific protein is glucose oxidase (GOx) and the mean size of the deposited gold nanoparticles is 14 nm±2 nm. In still other example embodiments consistent with the present invention, the specific protein is Casein and the mean size of the deposited gold nanoparticles is 40 nm±2 nm.

§ 3 BRIEF DESCRIPTION OF THE DRAWINGS

§ 4 DETAILED DESCRIPTION

Figure 1:
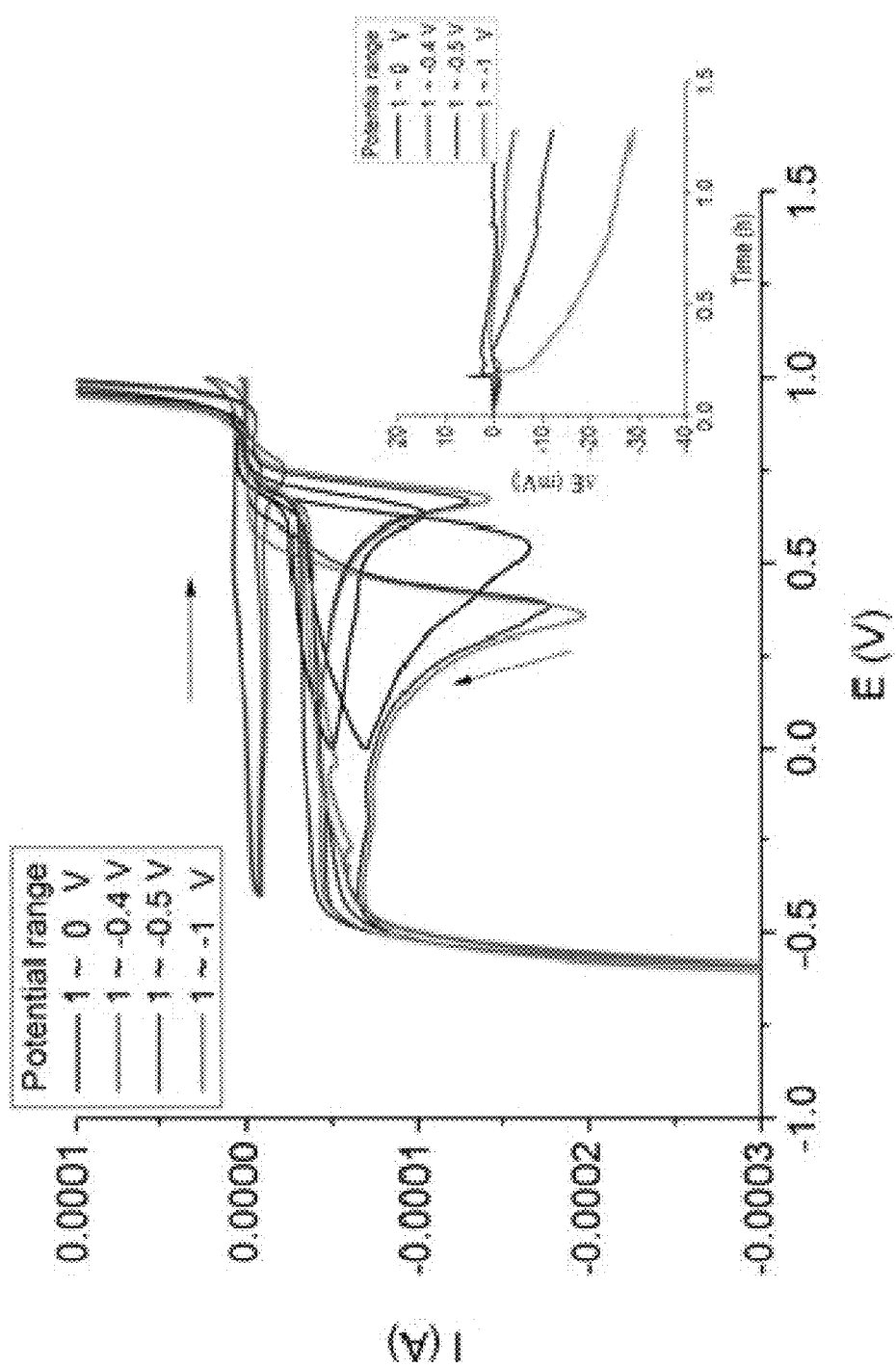
FIG. 1 illustrates cyclic voltammetry (CV) plots of GNPs' electrodeposition within different potential ranges, and potentiometric responses of BSA adsorption on the resulting electrodes.
Figure 2A:
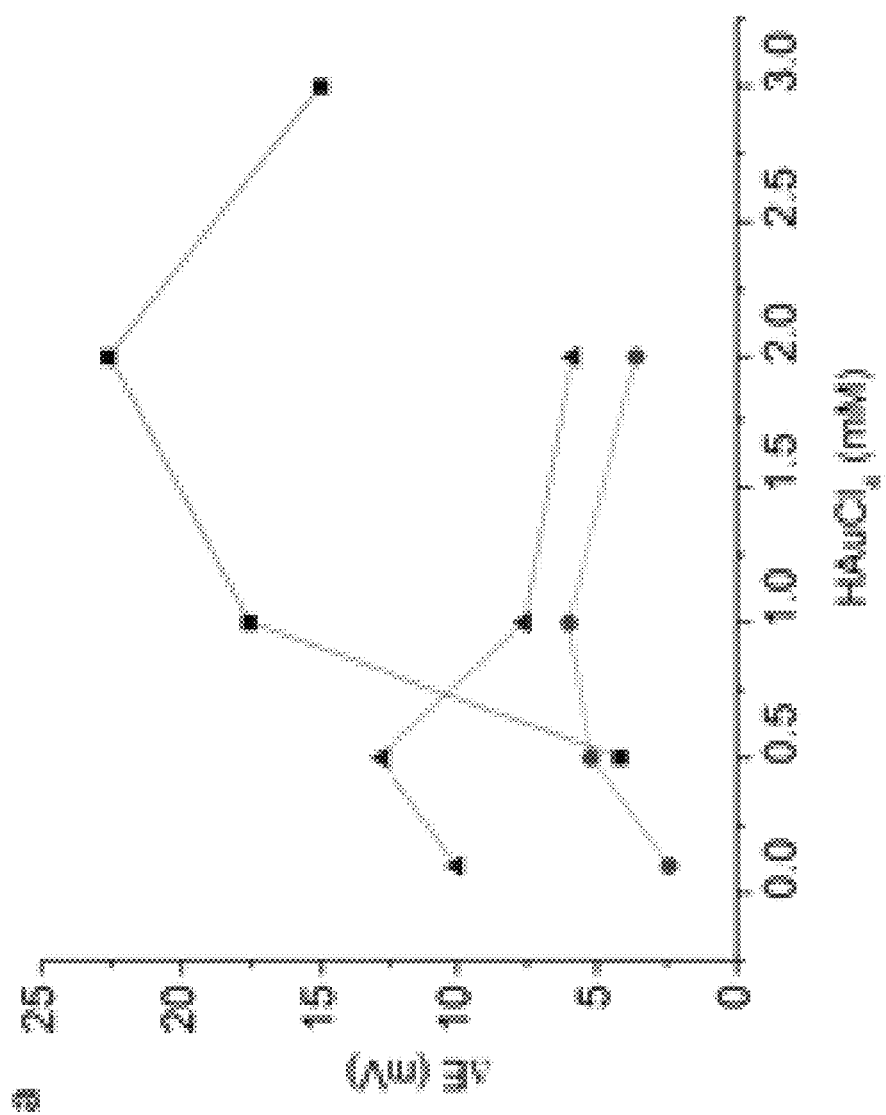
FIGS. 2A-2D are plots showing the effect of concentration of (a) $HAuCl_4$, (b) $H_2SO_4$, (c) scan cycles and (d) scan rates, respectively, on the response of a GNP modified GC electrode to 10 µg mL$^{-1}$ of BSA, GOx and casein adsorption.
Figure 2B:
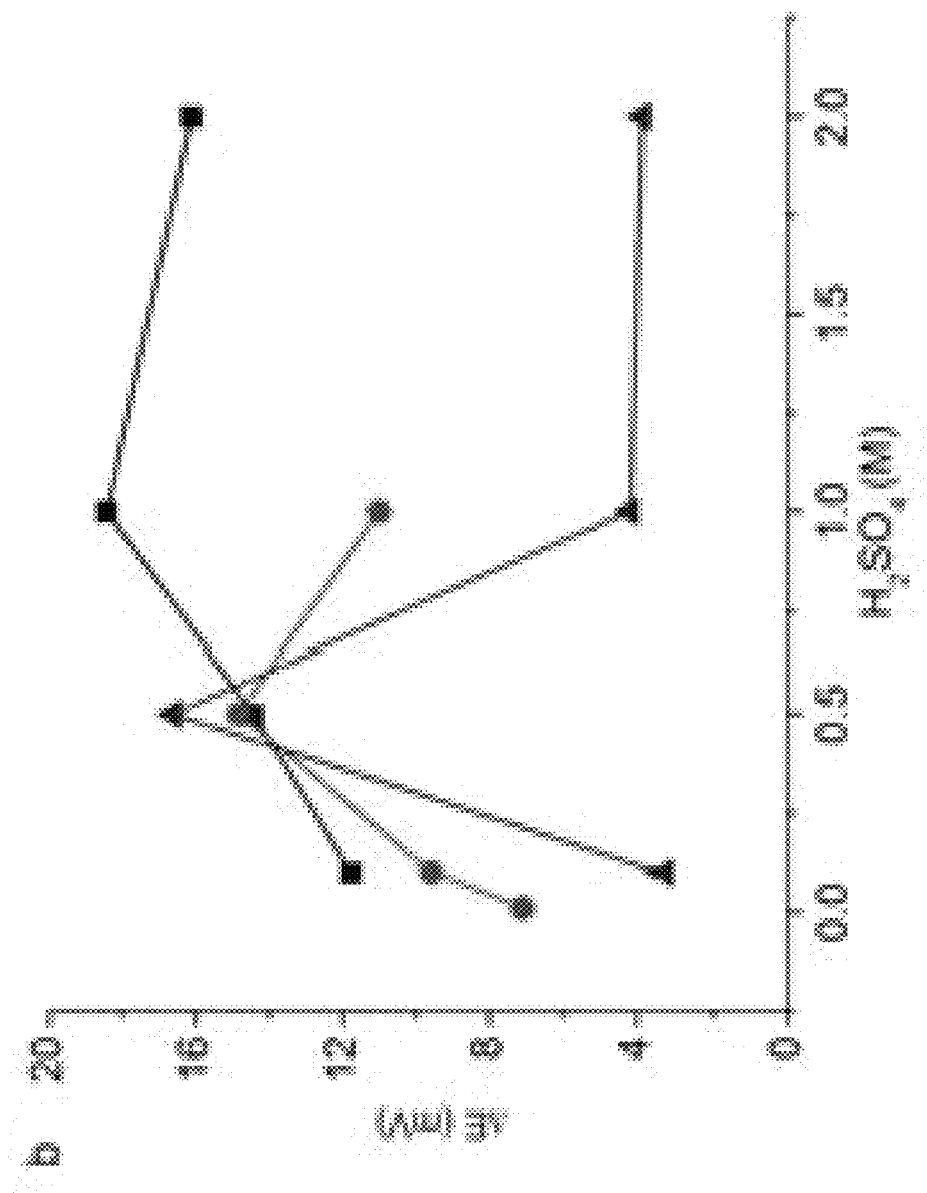
Figure 2C:
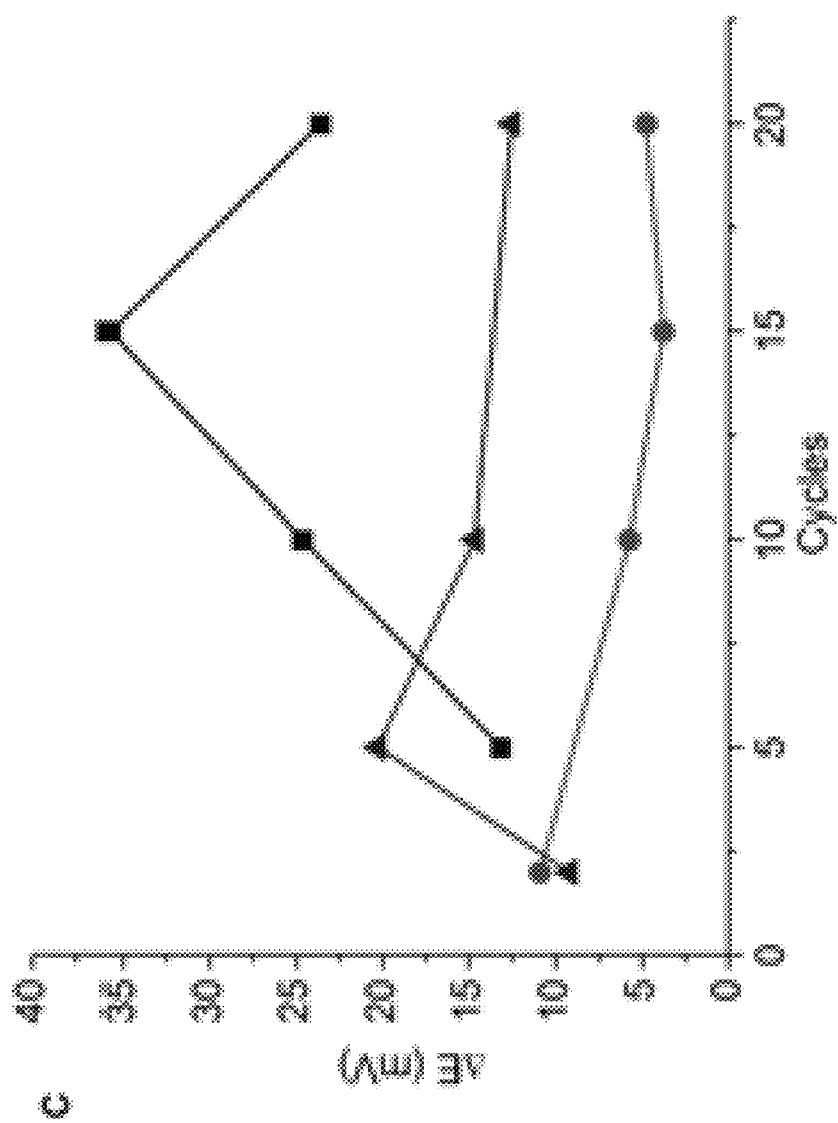
Figure 2D:
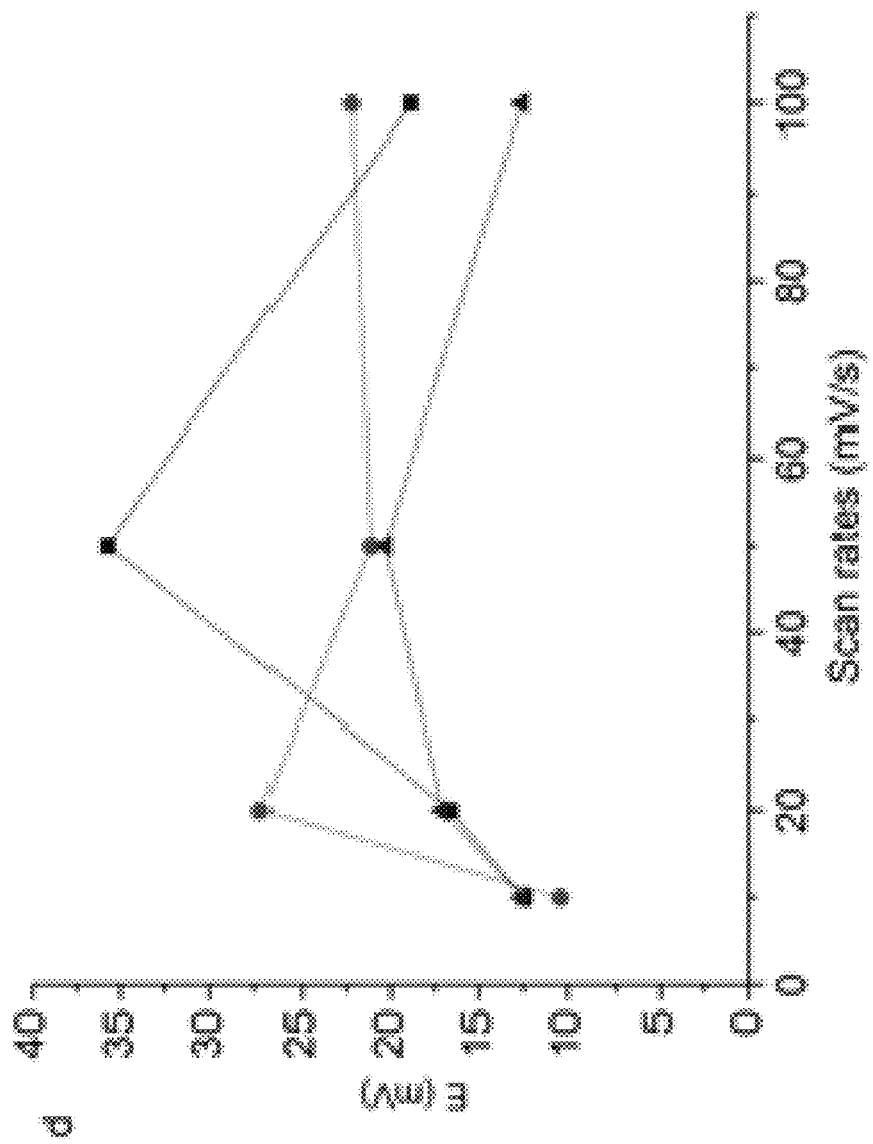

Example embodiments consistent with the present invention may involve novel methods, apparatus, and compositions of matter for potentiometric biosensing, and methods for making potentiometric biosensors. The following description is presented to enable one skilled in the art to make and use the invention, and is provided in the context of particular applications and their requirements. Thus, the following description of embodiments consistent with the present invention provides illustration and description, but is not intended to be exhaustive or to limit the present invention to the precise form disclosed. Various modifications to the disclosed embodiments will be apparent to those skilled in the art, and the general principles set forth below may be applied to other embodiments and applications. For example, although a series of acts may be described with reference to a flow diagram, the order of acts may differ in other implementations when the performance of one act is not dependent on the completion of another act. Further, non-dependent acts may be performed in parallel. No element, act or instruction used in the description should be construed as critical or essential to the present invention unless explicitly described as such. Also, as used herein, the article "a" is intended to include one or more items. Where only one item is intended, the term "one" or similar language is used. Thus, the present invention is not intended to be limited to the embodiments shown and the inventors regard their invention as any patentable subject matter described.

§ 4.1 EXAMPLE EXPERIMENTS

The following experiments test a new platform for high sensitivity potentiometric sensing. GNPs with different sizes were directly electrodeposited onto glassy carbon (GC) and indium tin oxide (ITO) film coated glass electrodes. The surfaces of the modified electrodes were characterized using Atomic Force Microscopy (AFM). The application of GNPs of different sizes modified electrodes were investigated for the potentiometric detection of different proteins.

§ 4.1.1 Materials and Methods Used in Example Experiments

§ 4.1.1.1 Materials

Gold (III) chloride trihydrate 99.9%, BSA, anti-BSA produced in rabbit, GOx, and casein were purchased from Sigma-Aldrich and used without further purification. All solutions were prepared in Milli-Q water (18 ΩM). A pH 7.4 phosphate-buffered saline (PBS) solution of 0.2 M disodium orthophosphate ($Na_2HPO_4$), 0.2 M sodium dihydrogen orthophosphate ($NaH_2PO_4$) was prepared. Before use, the PBS solution was diluted to 10 mM with Milli-Q water. This PBS solution was used as electrolyte solution for potentiometric detection, and to prepare various protein solutions, which were stored at 4° C. while not in use.

§ 4.1.1.2 Methods: Electrodeposition of GNPs

The fabrication of GNPs on a GC (3 mm dia., CH Instrument) or ITO (15-25 ohms, Delta Technologies, LTD) electrode was performed using electrochemical deposition. (See, e.g., the articles, Wang, Y., et al., "*Electrodeposition of Large Size Gold Nanoparticles on Indium Tin Oxide Glass and Application as Refractive Index Sensor,*" *Electrochemistry Communications*, 2009. 11(5): p. 1034-1037 and Zhao, Y., et al., "*Electrocatalytic Behavior and Amperometric Detection of Morphine on ITO Electrode Modified with Directly Electrode posited Gold Nanoparticles,*" *Electroanalysis*, 2009. 21(8): p. 939-943 (incorporated herein by reference).) A GC electrode was polished with aluminum oxide powder and electrochemically treated in 1 M $H_2SO_4$ solution to remove any organic binders and contamination that occurs at electrode surface. An ITO electrode was sequentially sonicated in acetone, ethanol, and distilled water (DI water) for 15 min. After cleaning, the GC or ITO electrode was immersed into the solution of $HAuCl_4$ in $H_2SO_4$. A cyclic voltammetric mode with the potential range of 1 V to −1 V was performed for electrodeposition. (See Results and Discussion in § 4.1.2 for details.) Then the electrode was quickly removed, washed with DI water and dried with a stream of nitrogen. The electrochemical experiments were performed by a CHI 660D electrochemical workstation (CH Instruments, Inc.) with a conventional three electrode system, including the GC or ITO electrode as working electrode, a Ag/AgCl electrode as the reference electrode and a platinum wire as the counter electrode.

§ 4.1.1.2 Methods: Potentiometric Detection

Potentiometric detection was performed by EMF interface instrument (Malvern, Pa.) for monitoring potential change simultaneously in real time. The GNPs-modified GC working electrode and the Ag/AgCl (1 M KCl) reference electrode were immersed into the PBS solution and the signal of potential change was recorded. After the potential signal was stable (less than 1 mV drift in 10 min), a series concentrations of proteins were added into the solution to check the signal changes.

§ 4.1.1.3 Methods: Atomic Force Microscopy

For imaging GNPs and proteins on the ITO surface, atomic force microscopy (AFM) experiments were performed with a multimode scanning probe microscope equipped with the type EV scanner and Nanoscope IIIa controller (Digital Instruments, Veeco). The tapping mode was employed under ambient air using an etched silicon probe (Bruke AFM probes, spring constant ~42 N m$^{-1}$, drive frequency 320 kHz). Data were recorded at a scan rate of 1-3 Hz, and stored in 256×256 pixel format. Images were processed using the Nanoscope version 4.43r8 software (Digital Instruments, Veeco). No processing was used on images obtained in the tapping mode, except for a flattening operation. For images to be used in measuring heights, only zero-order flattening was used. For image presentation, first-order flattening was used unless otherwise indicated.

§ 4.1.1.4 Methods: Glucose Detection to Demonstrate that GOx Remains Active on a GNP Plated Electrode The detection of glucose was performed in an electrochemical cell filled with 20 mM of 10 mM PBS at room temperature. In a steady-state amperometric experiment, the potential was set at 0.6 V under gentle magnetic stirring.

§ 4.1.2 Experimental Results and Discussion

§ 4.1.2.1 Optimization of Electrodeposition Efficiency

Electrodeposition of GNPs is a fast and convenient method of preparation. Various electrochemical methods, such as potential step, pulse techniques and cyclic voltammetry (CV) have been used for electrodeposition of GNPs. Here, the electrodeposition of GNPs on a GC electrode was been performed in $H_2SO_4$ acidic solution containing $HAuCL_4$ by the cyclic voltammetry method. FIG. 1 shows the CV plots of GNPs electrodeposition within different potential ranges. More specifically, FIG. 1 illustrates CV plots of GNPs electrodeposition within different potential ranges (scan cycle: 2 cycles; Scan rates: 50 mV $s^{-1}$). The inset of FIG. 1 are plots illustrating potentiometric responses of BSA adsorption on the resulting electrodes.

As seen, on the cathodic—going scan, the cathodic peak appeared at around 0.4 V and is due to reduction of gold (III) to gold. In the second cycle, this peak shifted to more positive potential. This indicates easier electrodeposition of gold on the existing gold particles. With scanning to more negative potentials, a sharp increase in reduction current at potential more negative than −0.5 V is attributed to the reduction of water, resulting in the formation of hydrogen gas. (See, e.g., the article, Moulton, S. E., et al., "*Investigation of Protein Adsorption and Electrochemical Behavior at a Gold Electrode,*" *Journal of Colloid and Interface Science* 2003. 261(2): p. 312-319 (incorporated herein by reference).) On the anodic—going scan, the peak at 1 V corresponds to the surface oxidation of the electro deposited gold. Our SEM and UV-vis spectrum results also confirmed that the GNPs were successfully deposited onto the surface of electrode with a quite symmetric distribution.

From the foregoing results, the present inventors found the electrodeposition of GNPs with different potential ranges exhibit different potentials of gold reduction peak, which move toward to a more negative potential gradually along with extending of the potential range from 1~0 V to 1~−0.4 V, 1~−0.5 V and 1~−1 V. (See FIG. 1.) The present inventors then detected the protein adsorption ability of these resulting GNPs-modified GC electrodes by potentiometric method. It seems that the more negative the potential applied during the electrodepositing, the more proteins the GNPs synthesized can load on their surface. (See the inset of FIG. 1.) These results suggest that a lower potential applied in GNPs electrodeposition is important. Roustom et. al. reported that when preparing nano-sized particles deposition onto an electrode, nucleation and growth are the basic processes that should be involved, (See, e.g., the article, Roustom, B. E., G. Fob, and C. Comninellis, "*Preparation of Gold Nanoparticles by Heat Treatment of Sputter Deposited Gold on Boron-Doped Diamond Film Electrode,*" *Electrochemistry Communications,* 2005. 7(4): p. 398-405 (incorporated herein by reference).) If the low potential is more positive than −0.4 V, it becomes hard to nucleate the gold. At potential more negative than −0.4 V, a nucleation with a sufficient large overpotential can be achieved to effectively seed the surface with nuclei. (See, e.g., the reference, Wang, Y., et al., "*Electrodeposition of Large Size Gold Nanoparticles on Indium Tin Oxide Glass and Application as Refractive Index Sensor,*" *Electrochemistry Communications,* 2009 11(5): p. 1034-1037 (incorporated herein by reference).) So in the following cycle, GNPs can start to grow on the surface of electrode. When the low potential is more negative, the processed of nucleation and growth may take place simultaneously. In these experiments, the present inventors applied −1 V potential to increase the growth rate of GNPs.

§ 4.1.2.2 Optimal Conditions for Protein Adsorption

For the mechanism of GNPs electrodeposition, it was confirmed that free gold (III) ions from solution will become attached to the surface of the electrode via electrostatic interaction first. Then, the application of potential to the electrode promoted the subsequent reduction of gold (III) ion. (See e.g., the article, Mohanty, U.S., "*Electrodeposition: A Versatile and Inexpensive Tool for the Synthesis of Nanoparticles, Nanorods, Nanowires, and Nanoclusters of Metals,*" *Journal of Applied Electrochemistry,* 2011 41(3): p. 257-270 (incorporated herein by reference).) The size and quantity of GNPs electrodeposited on the electrode surface depends on the gold (III) ion adsorbance and deposition time. The concentration of $HAuCl_4$, acidity of solution media, scan cycles and scan rate also have an effect on the size and film thickness of GNPs deposited. Here, the present inventors electrodeposited GNPs films on electrodes by cyclic voltammetry, and controlled the growth of nanoparticles size and film thickness with these different parameters. The present inventors chose three kinds of proteins, casein, GOx and BSA, which have different molecular weight but the similar value of pI. As all the pI's of BSA, GOx and casein are around 4.5, these proteins were negative charges in PBS buffer (pH 7.4). In this part, GNPs were electrodeposited with the different concentrations of $HAuCl_4$, acidic solution media, cycles and scan rates. The potentiometric method was used to evaluate the ability of the proteins to be immobilized on the surface of GNPs. The experiments by the present inventors found under which parameters the synthesized GNPs can adsorb proteins effectively.

FIGS. 2A-2D compare (a) the concentration of $HAuCl_4$ and (b) the concentration of $H_2SO_4$, (c) scan cycles and (d) scan rate, respectively, on the response of a GNPs-modified GC electrode toward to 10 μg $mL^{-1}$ of BSA (▲), GOx (●) and casein (■) adsorption. The maximum 10 μg mL-1 concentration of BSA adsorption on GNPs was observed when GNPs were electrodeposited in the solution containing 0.5 M $HAuCl_4$ (See FIG. 2A ▲.) and 0.5 M H2SO4 (See FIG. 2B ▲.) with 5 cycles (See FIG. 2c ▲.) at the scan rate of 50 mV s-1 (See FIG. 2d ▲.) This combination of CV parameters is referred to as "method 1".

In the following, the present inventors also detected the GOx and casein adsorption efficiency with different sizes and densities of GNPs. The present inventors found that the maximum of GOx bonding on GNPs was observed when GNPs was electrodeposited in the solution containing 1 mM $HAuCl_4$ (See FIG. 2A ●.) and 0.5 M $H_2SO_4$ (See FIG. 2B ●.) with 2 cycles (See FIG. 2C ●.) at the scan rate of 20 mV $s^{-1}$ (See FIG. 2A ●.). This combination of CV parameters is referred to as "method 2". Finally, the present inventors found the maximum of casein bonding on GNPs was observed when GNPs was electrodeposited in the solution containing 2 mM HAuCl$_4$ (See FIG. 2A ■.) and 1 M H$_2$SO$_4$ (See FIG. 2B ■.) with 15 cycles (See FIG. 2C ■.) at the scan rate of 50 mV s$^{-1}$ (See FIG. 2A ■.). This combination of CV parameters is referred to as "method 3".

The foregoing results indicate that different sizes of proteins have different adsorption ability with GNPs.

§ 4.1.2.3 Atomic Force Microscopy ("AFM") Results

Figure 3B:
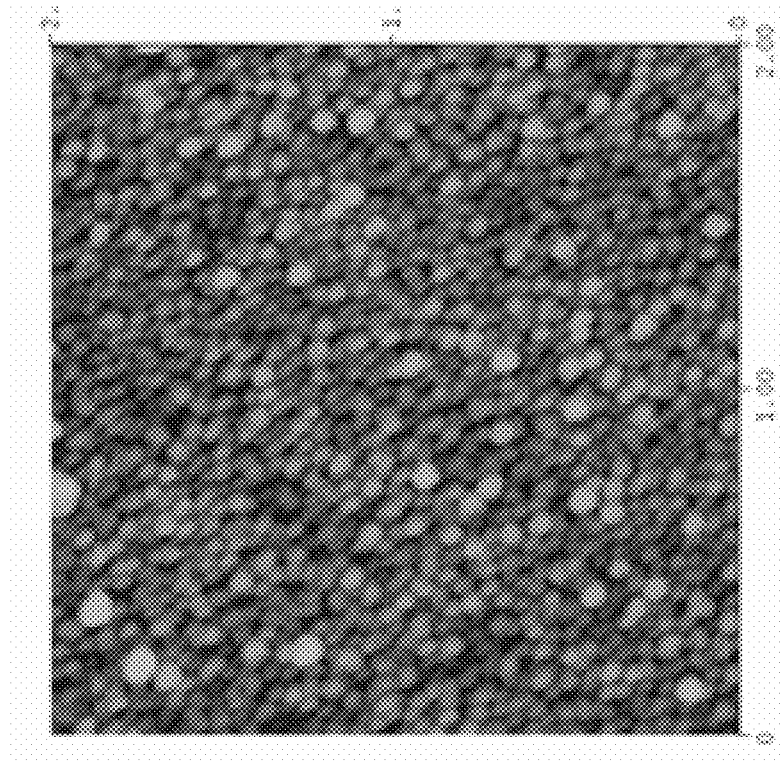
FIGS. 3A-3C are Atomic Force Microscopy (AFM) scans of GNPs electrodeposited with three (3) respective methods.
Figure 3A:
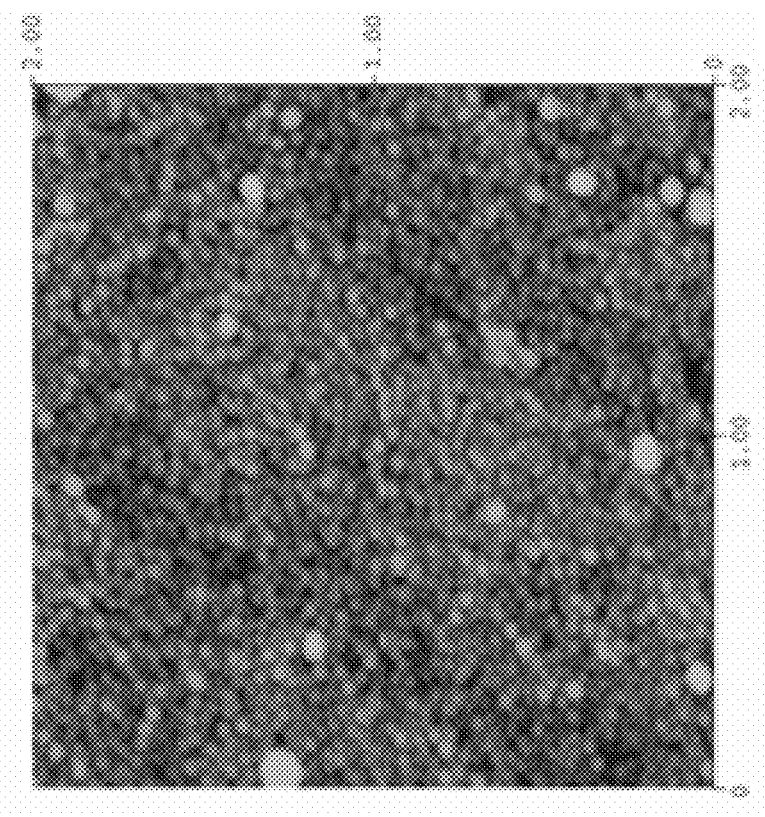

The morphologies of the modified electrodes were investigated using AFM. For the convenience of AFM operation, GNPs were electrodeposited on the ITO electrodes with methods 1, 2 and 3, described above. FIGS. 3A-3F are microphotographs of the AFM scans obtained over 2 μm×2 μm areas and plotted using the same scale in order to facilitate comparisons. The vertical scale ranges are from 0 to 50 nm (deep red to white). FIGS. 3A-3C show the film of GNPs electrodeposited using method 1, method 2 and method 3, respectively. Referring to FIGS. 3A-3C, note that films of GNPs were formed on the ITO surface. Line scan analysis was used to obtain the mean GNPs sizes, which were shown to be 5, 14 and 40 nm for the surfaces fabricated using methods 1, 2 and 3, respectively. These results indicate that the sizes of the synthesized GNPs depended on solution condition, cycles and scan rate. Thus, different GNP sizes could be made by the method of electrodeposition with different parameters.

Figure 3D:
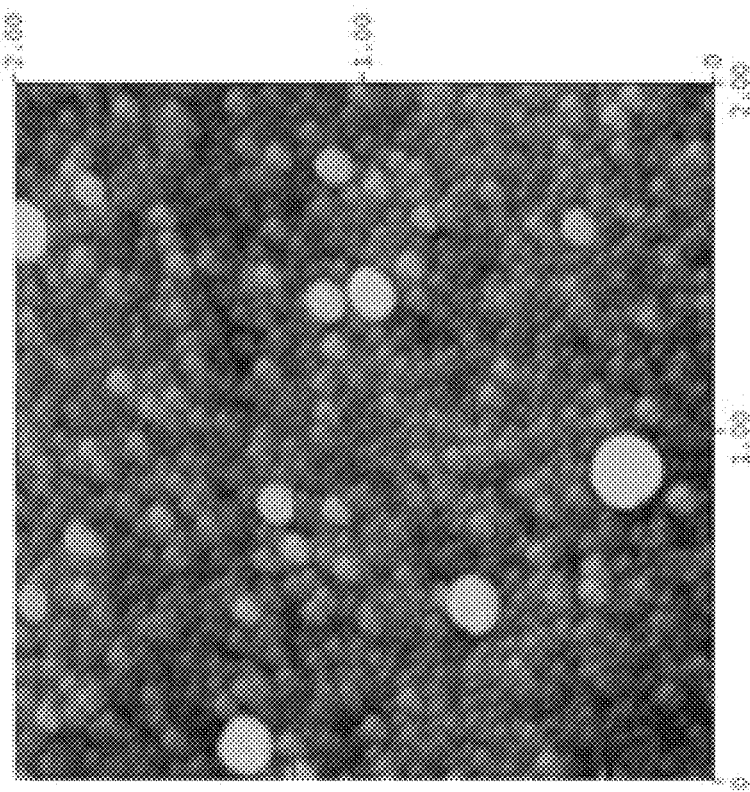
FIGS. 3D-3F are AFM scans of GNP electrodes coated with adsorbed proteins of BSA, GOx and casein, respectively.
Figure 3C:
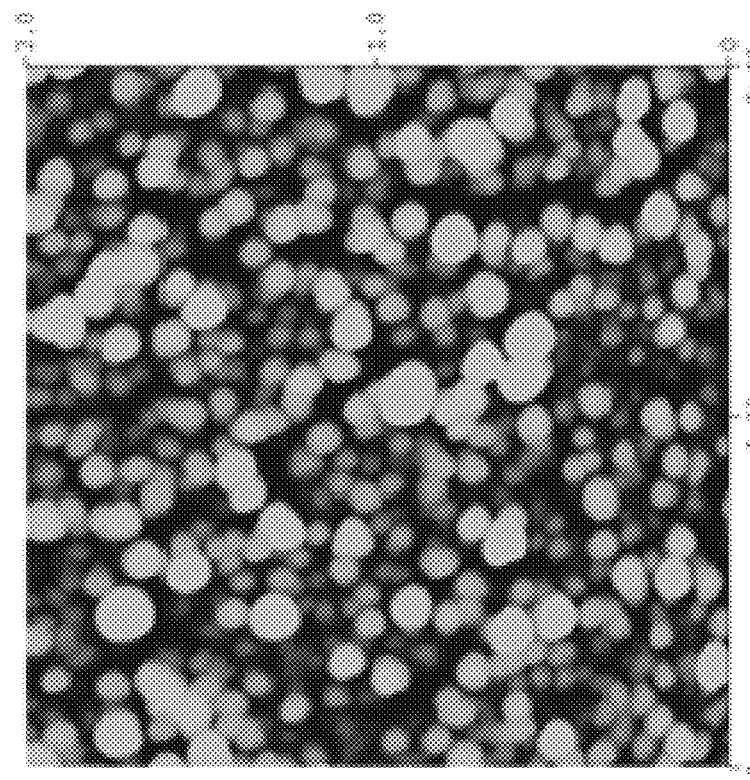
Figure 3F:
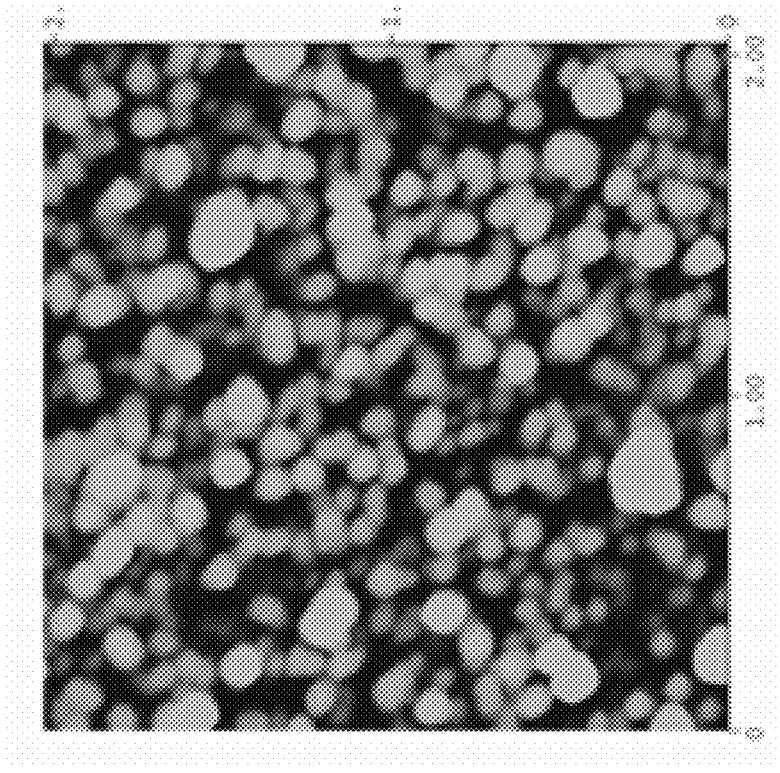
Figure 3E:
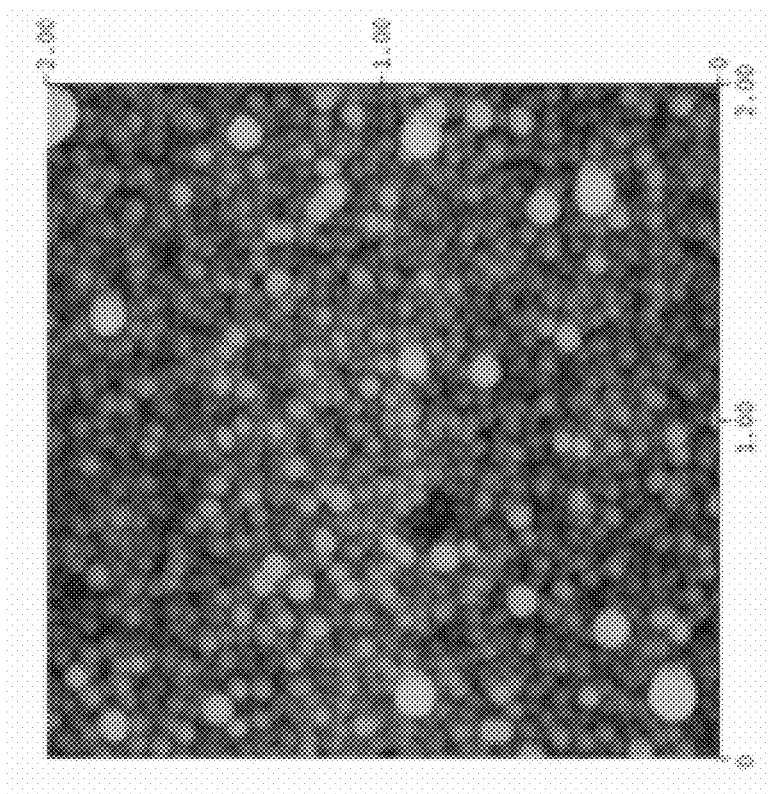
Figure 4:
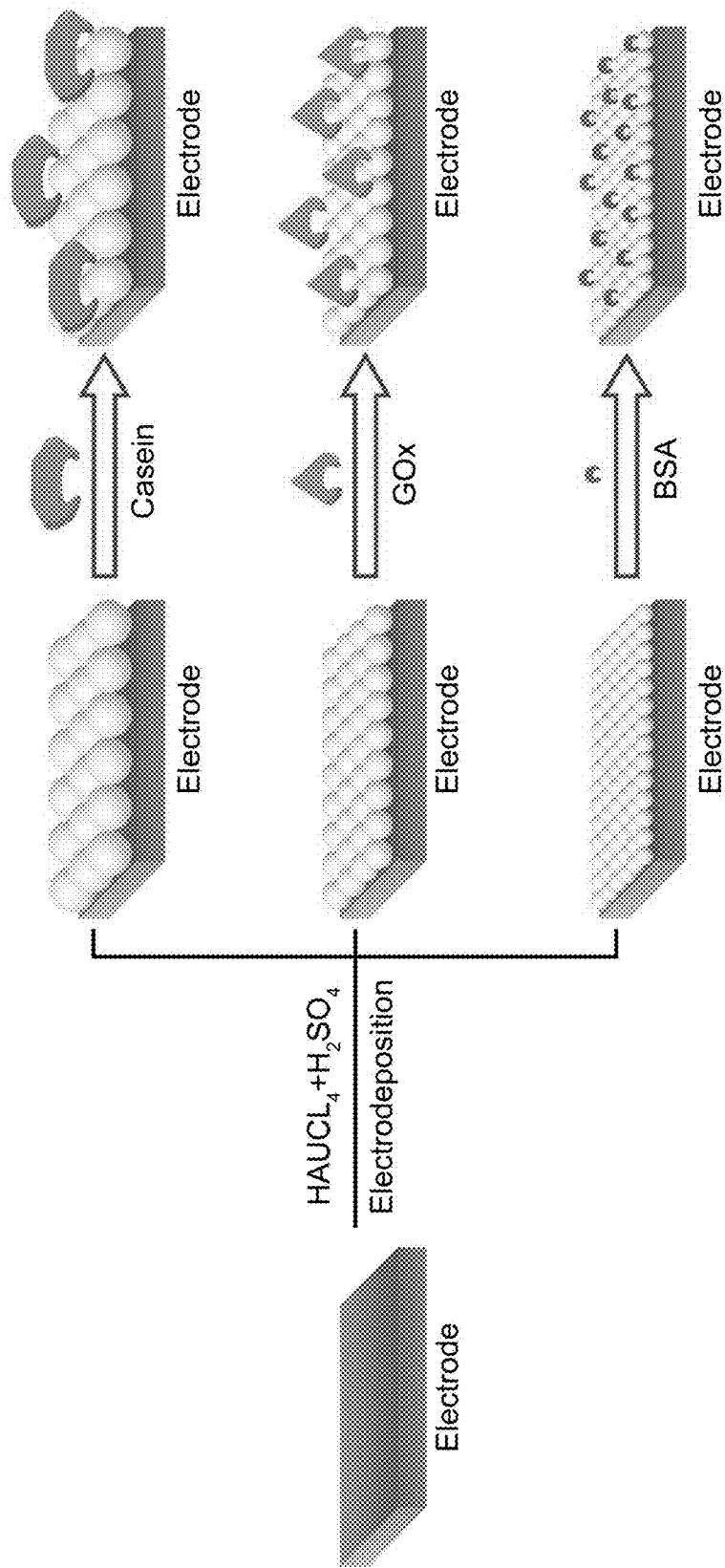
FIG. 4 is a schematic illustration of platforms formed of different sizes of GNPs, and the adsorption of different proteins.

FIGS. 3D-3F are AFM scans of GNPs electrodeposited with the proteins of BSA, GOx and casein, respectively. The AFM scans area were 2 μm×2 μm and the color scale of the scan range from 0-50 nm (deep red to white) Note that the adsorption of proteins were associated with the sizes of GNPs. The size of proteins studied are in the order of casein>GOx>BSA. The present inventors found that the smaller the protein, the easier their adsorption on smaller sizes of GNPs. (See, e.g., the scheme illustrated in FIG. 4 in which different sizes of GNPs formed platforms for the adsorption of different proteins.) After proteins adsorbed on those GNP modified surfaces, higher features and bigger particle sizes were observed (FIG. 3D-F). This result confirmed that the corona of the proteins formed on the surface of GNPs. On the basis of above results, the present inventors conclude that the protein adsorption on GNPs surface is size dependent.

§ 4.1.2.4 Potentiometric Detection

It is well known that there are three (3) mechanisms to explain the adsorption of protein to GNPs, namely: (1) electrostatic interaction of GNPs and opposite charged proteins; (2) covalent bonding between the thiols/amine group present within the amino acids in the protein and GNPs; and (3) hydrophobic interaction between proteins and GNPs. Global electrostatic effects may dominate when the protein is structurally stable and the solid surface is hydrophilic. (See, e.g., the article, Karnik, R., K. Castelino, and A. Majumdar, "*Field-Effect Control of Protein Transport in a Nanofluidic Transistor Circuit,*" *Applied Physics Letters,* 2006 88(12) (incorporated herein by reference).) As BSA, GOx and casein are negatively charged in the neutral PBS buffer (pH 7.4), the difference of electrostatic interactions between proteins and GNPs can be neglected given their similar pI values (that is, 4.2, 4.6 and 4.8).

Figure 5:
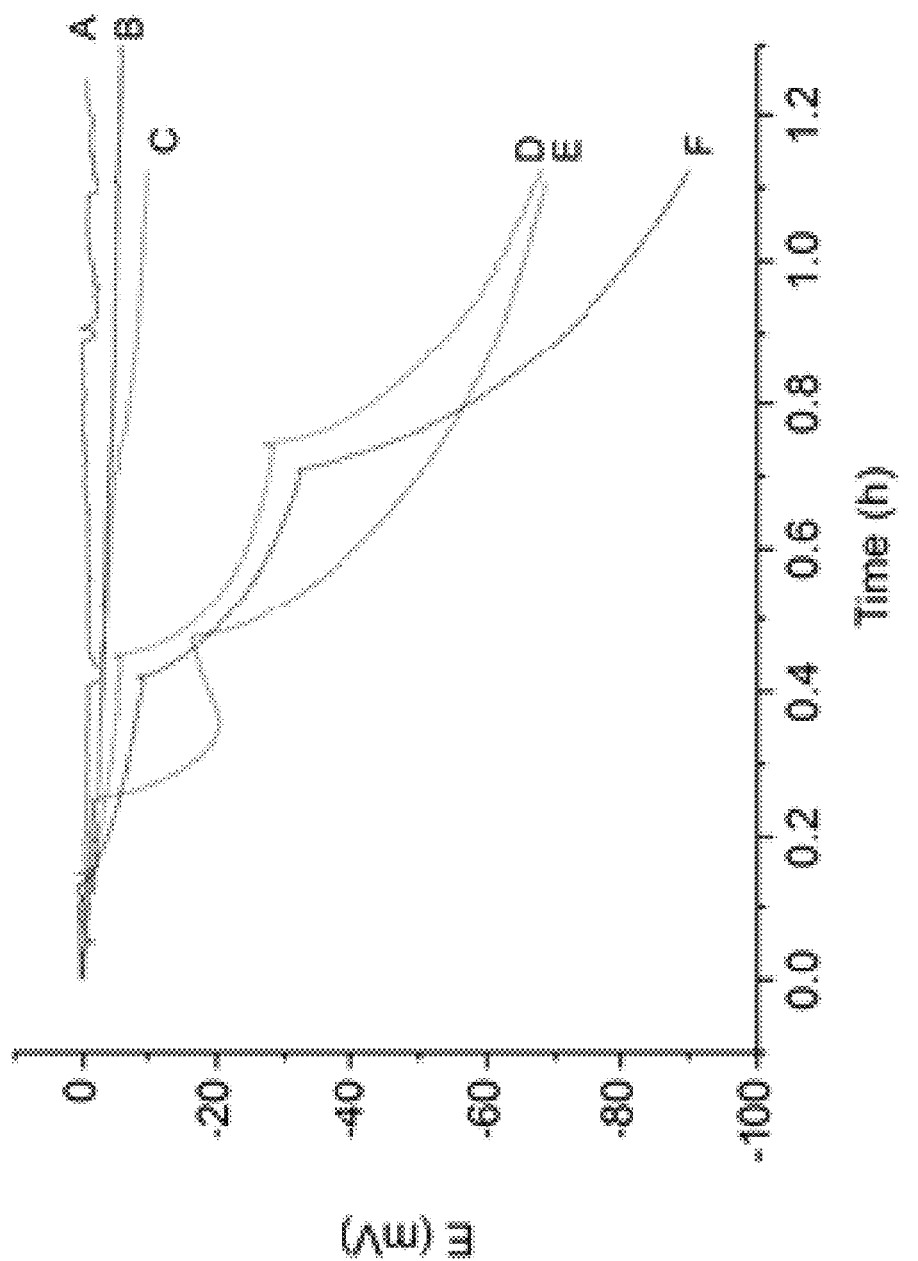
FIG. 5 illustrates potentiometric responses to BSA, GOx and casein adsorption on both (1) non-modified electrodes, and (2) GNP-modified GC electrodes.

To verify the signal amplification by GNPs, the present inventors compared the potentiometric response of these three kinds of proteins adsorption on both (1) GC electrodes and (2) GNPs-modified GC electrodes. In FIG. 5, potentiometric responses to GOx, BSA and casein adsorption on the non-modified electrodes are shown in plots A, B and C, respectively. Still referring to FIG. 5, potentiometric responses to GOx, BSA, and casein adsorption on the GNPs-modified GC electrodes are shown in plots D, E and F, respectively. In each case, 1, 10, and 100 μg mL$^{-1}$ of BSA, GOx or casein were added in series.

Referring to plots A-C of FIG. 5, note that when the proteins were added in series (at 1, 10, and 100 μg mL$^{-1}$ as described above), there was almost no potential change with the non-modified GC electrode. It is assumed that small amounts of proteins adsorption on GC electrode occurs, or because of the poor conductivity of GC, it is hard to sense the potential response when protein adsorption occurs. On the other hand, plots D-F of FIG. 5 show the potentiometric response of these three kinds of GNPs-modified GC electrodes (prepared using methods 1-3). When the GNPs-modified electrodes contact with proteins solutions, negative shift of the potential was instantly observed and continued stepwisely with the increase in protein concentration (at 1, 10, and 100 μg mL$^{-1}$ as described above). The potential responses were caused by the contribution of adsorbed proteins. A comparison of plots A-C with plots D-F demonstrates that the GNPs (1) form an excellent platform for increased protein loading, and (2) efficiently improve the charge transfer between analyte and the electrode surface. The results also indicated that different kinds of proteins have different bonding behavior with GNPs, which is size dependent.

§ 4.1.2.5 Surface Activity of Proteins on GNPs Surface

Proteins are highly surface active and they interact with solid-liquid interfaces mainly through three subprocesses, namely: (1) structural rearrangement in the protein molecule; (2) dehydration of parts of protein and surface hydrophobic effect; and (3) redistribution charged group in the interfacial layer. (See, e.g., the article, Karnik, R., K. Castelino, and A. Majumdar, "*Field-Effect Control of Protein Transport in a Nanofluidic Transistor Circuit,*" *Applied Physics Letters,* 2006 88(12) (incorporated herein by reference).) If proteins bond to the solid surface, most of proteins will undergo denaturation of their tertiary structure, and their secondary structure could also be disrupted in some cases. The present inventors evaluated the activity of BSA and GOx after they were adsorbed on the surfaces of GNPs.

Figure 6A:
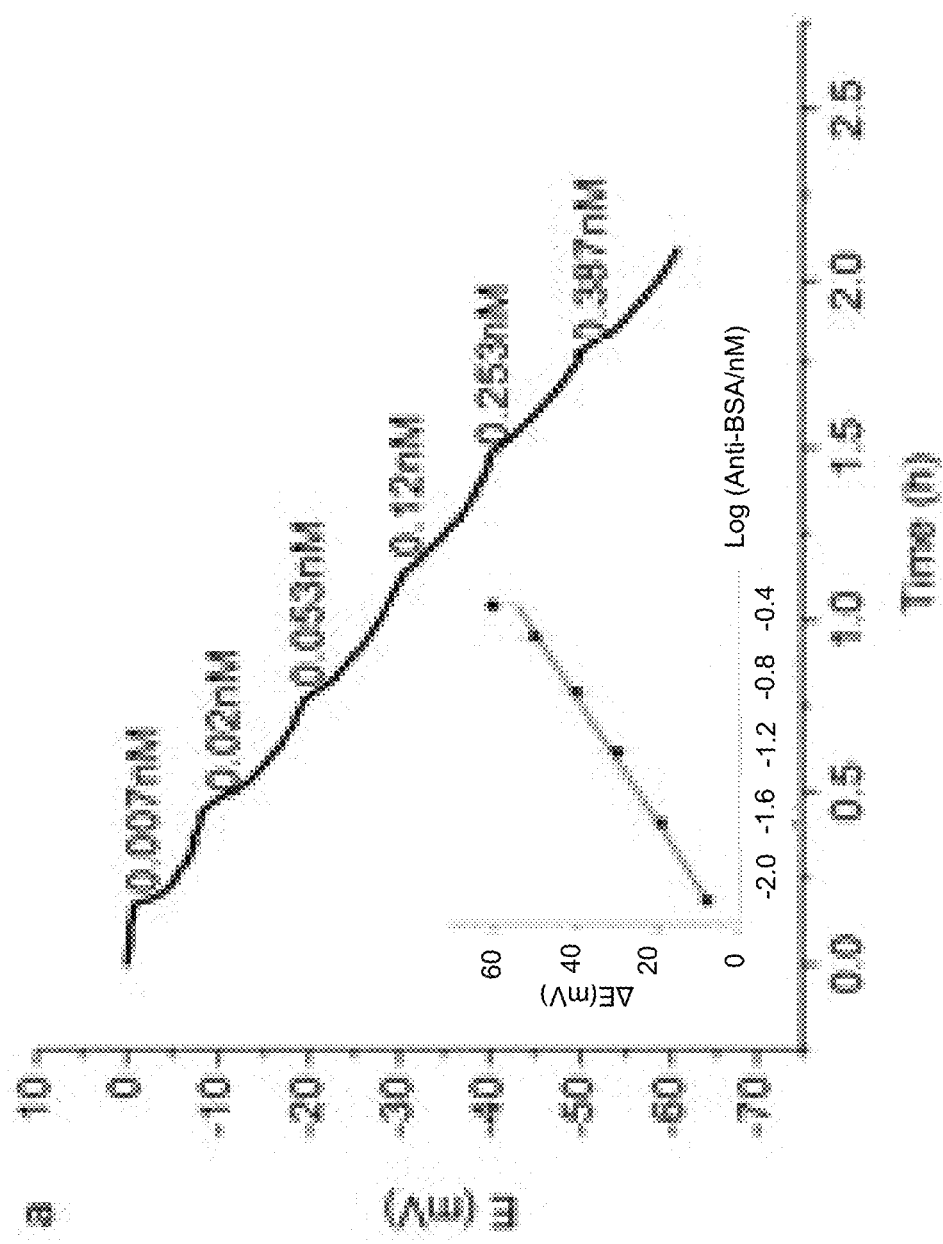
FIGS. 6A and 6B illustrate a potentiometric response of anti-BSA bonding on the GC, GNP and BSA modified electrode and an Amperometric response of the GC, GNP and GOx modified electrode, respectively, upon successive addition of glucose at the potential of 0.6V.
Figure 6B:
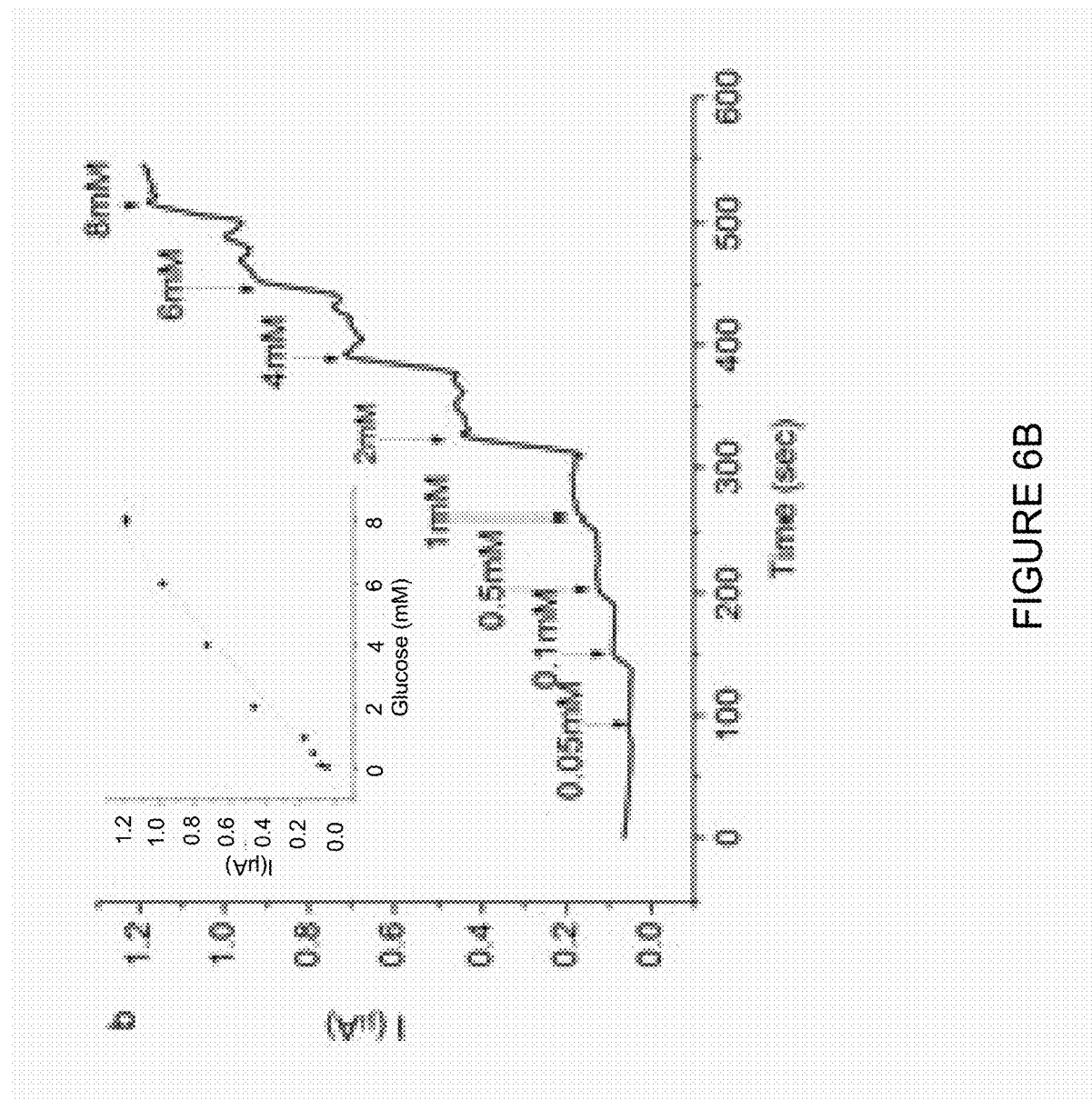

FIG. 6A is a plot illustrating a potentiometric response of anti-BSA bonding on the GC/GNPs/BSA modified electrode. The inset of FIG. 6A is a calibration curve, of potential change vs. log of ant-BSA concentration. FIG. 6B is a plot illustrating amperometric response of the GC/GNPs/GOx modified upon successive addition of glucose at the potential of 0.6V. The inset of FIG. 6B is a current change vs. glucose concentration curve.

More specifically, FIG. 6A shows the anti-BSA interacting with BSA which was adsorbed on the GNPs-modified electrode surface. In this experiment, PEG-thiol was used as a blocking reagent for blocking the non-specific adsorption. After BSA was adsorbed on the GNP surfaces, PEG-thiol molecules were immobilized onto the GNPs surface via gold-thiol linkage to prevent the unbound sites from reacting with the subsequently added the analyte of anti-BSA proteins. From the results, fast and large signal responses were observed as shown in FIG. 6A. A linear relationship between the potential shift and logarithm of anti-BSA concentration was found from 0.007 nm to 0.387 nM (See the inset of FIG. 6A.) and with a detection limit of 3 pM. Table 1, presented later, lists the linear range and limit of detection obtained by the potentiometric techniques reported in the literature and by the reliable quantitative detection used by the present inventors. In comparison with the other types of potentiometric biosensors, the present inventors' method exhibits the widest linear range and lowest detection limit without additional labeling.

GOx can catalyze the oxidation of β-D-glucose to D-glucono-δ-lactone and hydrogen peroxide which then can be detected by an amperometric method. FIG. 6B illustrates a typical steady-state response of GOx/GNPs modified GC electrode on successive addition of different concentration of glucose. It presents a linear response to gluconse concentration within the range from 0.05 mM to 8 mM and a high sensitivity of $2.08 \times 10^{-3}$ A $M^{-1}$ $cm^{-2}$ (R=0.98). The remarkable current increase confirmed that GOx kept its activity on the GNPs surface.

As demonstrated in FIGS. 6A and 6B, using GNPs-modified electrodes made in accordance with the present invention, BSA and GOx were able to retain their native-like structure. The high sensitivity of this detection can be attributed to the GNPs, which provide the biocompatible microenvironment to maintain the activity of the protein and greatly enhance the conductivity.

TABLE 1

Comparison of potentiometric biosensors for detection of proteins

| Type of protein | Assay principle | Linear range (nM) | Detection limit (nM) | Reference |
|---|---|---|---|---|
| Anti-BSA | GNPs electro-depositon on electrode surface | 0.007-0.387 | 0.003 | Our result |
| Human immunoglobulin G | Functionalized Fe3O4 nanoparticles immobilized on electrode surface | 0.006-0.08 | 0.002 | (See, e.g., the article, Li, J. P. and H. D. Gao, "A Renewable Potentiometric Immunosensor Based on Fe3O4 Nanoparticles Immobilized Anti-IgG," Electroanalysis, 2008. 20(8): p. 881-887 (incorporated herein by reference).) |
| Hepatitis B surface antigen | Enzyme labeled secondary antibody-gold nanoparticles (GNPs) bio-conjugates | 0.0007-0.067 | 0.0002 | (See, e.g., the article, Ding, C. F., et al., "Electrochemical Immunoassay of Hepatitis B Surface Antigen by the Amplification of Gold Nanoparticles Based on the Nanoporous Gold Electrode," Talanta, 2010. 80(3): p. 1385-1391 (incorporated herein by reference).) |
| Thrombin | SWCNTas transducers, and aptamers as bio-recognition elements | 100-1000 | 80 | (See, e.g., the article, Duzgun, A., et al., "Solid-Contact Potentiometric Aptasensor Based on Aptamer Functionalized Carbon Nanotubes for the Direct Determination of Proteins," Analyst, 2010. 135(5): p. 1037-1041 (incorporated herein by reference).) |
| Mouse IgG | GNPs labeled antibody for signal amplification | 3-45 | 0.013 | (See, e.g., the article, Chumbimuni-Torres, K. Y., et al., "Potentiometric Biosensing of Proteins with Ultrasensitive Ion-Selective Microelectrodes and Nanoparticle Labels," Journal of the American Chemical Society, 2006. 128(42): p. 13676-13677 (incorporated herein by reference).) |

§ 4.3 Refinements, Alternative and Extensions

Although the foregoing examples concerned adjusting the average size of gold nanoparticles by properly setting parameters of cyclic voltemmetry electrodeposition, the size of other types of nanoparticles can be adjusted or set using the same or other techniques using the foregoing description and the following guidance. The desired result is to produce a nanoparticle surface in which an average size of the nanoparticles facilitates immobilization of a desired protein on the nanoparticle surface without denaturing the protein such that the protein remains active after it is immobilized. This can be accomplished when one considers the relationship between (1) the size of the protein at the anchoring point(s), and (2) the size and curvature of the nanoparticles. One may also consider how the protein is immobilized on the nanoparticle layer (e.g., by physisorption (e.g., electrostatic, hydrophobic, van der Waals, physical encapsulation or entrapment, and/or hydrogen bonding), bioaffinity interaction, or covalent bonding). In the foregoing examples, the inventors believe the proteins were immobilized on the gold nanoparticles due to covalent bonding, electrostatic forces, and hydrophopic attraction.

Although gold nanoparticles were used in the examples provided above, the present invention extends to other nanoparticles (such as platinum, palladium, copper, metal oxide, etc.). Although conducting nanoparticles should be used in potentiometric biosensors, non-conducting nanoparticles can be used in other types of biosensors.

Although electrodepositing was used in the examples provided above, other techniques for depositing the nanoparticles onto an electrode or other biosensor surface can be used instead.

§ 4.4 CONCLUSION

The present inventors were able to make potentiometric biosensors, each with high sensitivity, by electrodepositing gold nanoparticles (GNPs). The adsorption of three model proteins with different sizes—BSA, GOx and casein—on the surfaces of GNPs-modified electrodes were investigated, and the present inventors found that GNP sizes played important role on proteins adsorption. Different sizes of proteins have different bonding with GNPs, which is size dependent. Real-time measurement of antibody adsorption onto the immobilized antigen was also detected using the resulting biosensors. A low detection limit of 3 pM and a linear range from 0.007 nm to 0.387 nM were achieved without a label step typically used in other techniques.

What is claimed is:

1. A method for making a potentiometric biosensor including a specific protein adsorbed onto gold nanoparticles, the method comprising:
    a) electrodepositing gold onto an electrode to produce a gold nanoparticle modified electrode, wherein the electrodepositing uses electrodeposition parameters selected to deposit gold nanoparticles on the electrode such that a mean size of the deposited gold nanoparticles corresponds to a size promoting, relative to other mean sizes of deposited gold nanoparticles produced by other combinations of electrodeposition parameters, adsorption of the specific protein onto the gold nanoparticles; and
    b) adsorbing the specific protein onto the gold nanoparticle electrode to produce the potentiometric biosensor, wherein the specific protein selected from a group consisting of (A) Bovine serum albumin (BSA), (B) glucose oxidase (GOx), and (C) Casein, and wherein if the specific protein is BSA, then the mean size of the deposited gold nanoparticles is 5 nm±2 nm, if the specific protein is GOx, then the mean size of the deposited gold nanoparticles is 14 nm±2 nm, and if the specific protein is Casein, then the mean size of the deposited gold nanoparticles is 40 nm±2 nm.

2. The method of claim 1 wherein the act of electrodepositing is performed using cyclic voltemmetry electrodeposition.

3. The method of claim 2 wherein at least one of the electrodepostion parameters is a voltage scan rate.

4. The method of claim 2 wherein at least one of the electrodepostion parameters is a maximum number of scan cycles.

5. The method of claim 1 wherein the electrodepositing uses electrodeposition parameters selected to deposit gold nanoparticles on the electrode such that a mean size of the deposited gold nanoparticles corresponds to a size optimizing, relative to other mean sizes of deposited gold nanoparticles produced by other combinations of electrodeposition parameters, adsorption of the specific protein onto the gold nanoparticles.

6. A method for making a potentiometric biosensor including a specific protein adsorbed onto gold nanoparticles, the method comprising:
    a) electrodepositing gold onto an electrode to produce a gold nanoparticle modified electrode, wherein the electrodepositing uses electrodeposition parameters selected to deposit gold nanoparticles on the electrode such that a mean size of the deposited gold nanoparticles corresponds to a size promoting, relative to other mean sizes of deposited gold nanoparticles produced by other combinations of electrodeposition parameters, adsorption of the specific protein onto the gold nanoparticles; and
    b) adsorbing the specific protein onto the gold nanoparticle electrode to produce the potentiometric biosensor, wherein the act of electrodepositing is performed using cyclic voltemmetry electrodeposition, and
    wherein at least one of the electrodepostion parameters is acidic solution concentration.

7. A potentiometric biosensor comprising:
    a) an electrode;
    b) gold nanoparticles coating a surface of the electrode; and
    c) a specific protein adsorbed onto the gold nanoparticles, wherein a mean size of the gold nanoparticles is one that promoted, relative to other mean sizes of deposited gold nanoparticles produced by other combinations of electrodeposition parameters, the adsorption of the specific proteins,
    wherein the specific protein selected from a group consisting of (A) Bovine serum albumin (BSA), (B) glucose oxidase (GOx), and (C) Casein, and
    wherein if the specific protein is BSA, then the mean size of the deposited gold nanoparticles is 5 nm±2 nm, if the specific protein is GOx, then the mean size of the deposited gold nanoparticles is 14 nm±2 nm, and if the specific protein is Casein, then the mean size of the deposited gold nanoparticles is 40 nm±2 nm.

8. The potentiometric biosensor of claim 7 wherein the specific protein remains active after its adsorption onto the gold nanoparticles.

9. The potentiometric biosensor of claim 7 wherein the specific protein is not denatured by its adsorption onto the gold nanoparticles.

10. The potentiometric biosensor of claim 7 wherein a mean size of the gold nanoparticles is one that optimized, relative to other mean sizes of deposited gold nanoparticles produced by other combinations of electrodeposition parameters, the adsorption of the specific proteins.

* * * * *